(12) United States Patent
Tannhauser et al.

(10) Patent No.: US 11,000,280 B2
(45) Date of Patent: May 11, 2021

(54) RECESSED SURGICAL FASTENING DEVICES

(71) Applicant: Ethicon, Inc., Somerville, NJ (US)

(72) Inventors: Robert J. Tannhauser, Bridgewater, NJ (US); Emil Richard Skula, Wayne, NJ (US)

(73) Assignee: Ethicon, Inc., Somerville, NJ (US)

( * ) Notice: Subject to any disclaimer, the term of this patent is extended or adjusted under 35 U.S.C. 154(b) by 67 days.

(21) Appl. No.: 16/042,201

(22) Filed: Jul. 23, 2018

(65) Prior Publication Data

US 2018/0325518 A1 Nov. 15, 2018

Related U.S. Application Data

(63) Continuation of application No. 14/082,432, filed on Nov. 18, 2013, now Pat. No. 10,052,105.

(51) Int. Cl.
| | | |
|---|---|---|
| *A61B 17/08* | (2006.01) | |
| *A61F 2/00* | (2006.01) | |
| *A61B 17/04* | (2006.01) | |
| *A61B 17/064* | (2006.01) | |
| *A61B 17/072* | (2006.01) | |
| *A61B 17/00* | (2006.01) | |

(52) U.S. Cl.
CPC .......... *A61B 17/08* (2013.01); *A61B 17/0401* (2013.01); *A61B 17/064* (2013.01); *A61B 17/07292* (2013.01); *A61F 2/0063* (2013.01); *A61B 2017/00004* (2013.01); *A61B 2017/0406* (2013.01); *A61B 2017/0412* (2013.01); *A61B 2017/0647* (2013.01)

(58) Field of Classification Search
CPC .............. A61B 17/0401; A61B 17/064; A61B 17/07292; A61B 2017/0406; A61B 2017/0412; A61F 2/0063
See application file for complete search history.

(56) References Cited

U.S. PATENT DOCUMENTS

| | | | |
|---|---|---|---|
| 4,754,758 A | * | 7/1988 | Li .......................... A61B 17/04 606/213 |
| 5,011,494 A | | 4/1991 | Von Recum et al. |
| 5,203,864 A | * | 4/1993 | Phillips ................ A61B 17/064 227/137 |
| 7,331,199 B2 | | 2/2008 | Ory et al. |
| 7,686,822 B2 | | 3/2010 | Shayani |
| 7,762,998 B2 | | 7/2010 | Birk et al. |
| 8,215,310 B2 | | 7/2012 | Browning |
| 8,409,224 B2 | | 4/2013 | Shriver |
| 8,617,183 B2 | | 12/2013 | Schneider et al. |

(Continued)

FOREIGN PATENT DOCUMENTS

| | | |
|---|---|---|
| DE | 19701985 A1 | 7/1998 |
| EP | 0783270 | 6/2004 |

(Continued)

*Primary Examiner* — Alexander J Orkin
(74) *Attorney, Agent, or Firm* — David R. Crichton

(57) ABSTRACT

Novel recessed surgical fastening devices are disclosed. The fastening devices have a compressible member and a fastening element disposed at least partially within the compressible member. The fastening element has at least one tissue engagement member that is extensible through the compressible member to engage tissue when a force is applied to the fastening device.

18 Claims, 10 Drawing Sheets

(56) References Cited

U.S. PATENT DOCUMENTS

| | | |
|---|---|---|
| 10,052,105 B2 | 8/2018 | Tannhauser et al. |
| 2003/0069603 A1 | 4/2003 | Little et al. |
| 2005/0244455 A1 | 11/2005 | Greenawalt |
| 2005/0283189 A1 | 12/2005 | Rosenblatt |
| 2006/0015144 A1* | 1/2006 | Burbank ............ A61B 17/064 606/219 |
| 2006/0100649 A1 | 5/2006 | Hart |
| 2006/0190039 A1 | 8/2006 | Birk |
| 2007/0260278 A1* | 11/2007 | Wheeler ............ A61B 17/0643 606/220 |
| 2008/0125869 A1 | 5/2008 | Paz |
| 2008/0140095 A1* | 6/2008 | Smith ............ A61B 17/00234 606/151 |
| 2008/0172088 A1* | 7/2008 | Smith .................. A61B 17/064 606/219 |
| 2009/0030435 A1 | 1/2009 | Burnett et al. |
| 2009/0182352 A1* | 7/2009 | Paz .................... A61B 17/0643 606/143 |
| 2009/0204130 A1* | 8/2009 | Kantsevoy ......... A61B 17/0401 606/151 |
| 2009/0206127 A1* | 8/2009 | Danielson ............ A61B 17/064 227/175.1 |
| 2009/0216233 A1* | 8/2009 | Wiedrich ............. A61B 17/064 606/75 |
| 2009/0254103 A1 | 10/2009 | Deutsch |
| 2010/0241161 A1 | 9/2010 | Heftman |
| 2010/0331880 A1 | 12/2010 | Stopek |
| 2011/0130774 A1* | 6/2011 | Criscuolo ............ A61F 2/0063 606/151 |
| 2011/0172760 A1 | 7/2011 | Anderson |
| 2011/0238094 A1 | 9/2011 | Thomas et al. |
| 2012/0080336 A1 | 4/2012 | Shelton, IV et al. |
| 2012/0283510 A1 | 11/2012 | Alexander |
| 2013/0158554 A1 | 6/2013 | Euteneuer et al. |
| 2013/0190817 A1 | 7/2013 | Bouduban et al. |
| 2013/0256375 A1 | 10/2013 | Shelton, IV et al. |

FOREIGN PATENT DOCUMENTS

| | | |
|---|---|---|
| EP | 1728473 A1 | 12/2006 |
| EP | 2229918 | 9/2010 |
| JP | 2007518446 | 7/2007 |
| JP | 2007530140 | 11/2007 |
| JP | 2012512715 | 6/2012 |
| JP | 2013531510 | 8/2013 |
| WO | WO 2013082581 | 6/2013 |
| WO | WO 2015073241 A1 | 5/2015 |

* cited by examiner

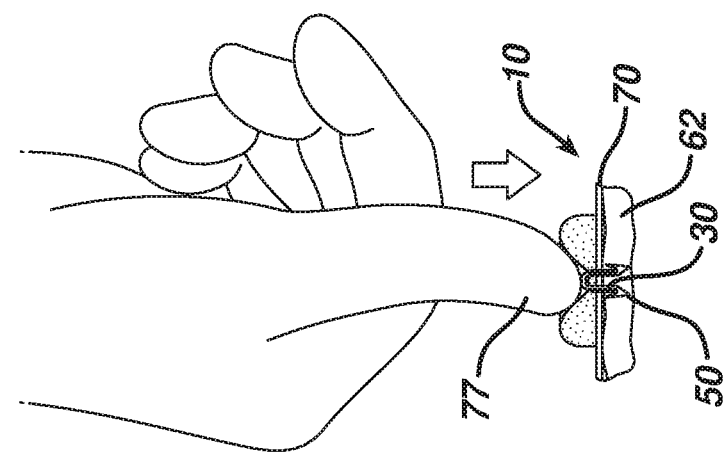
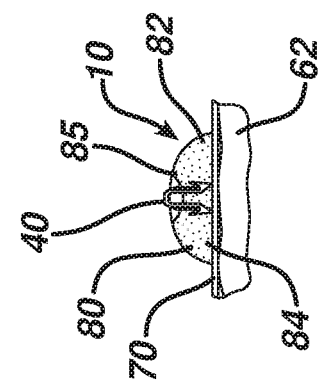
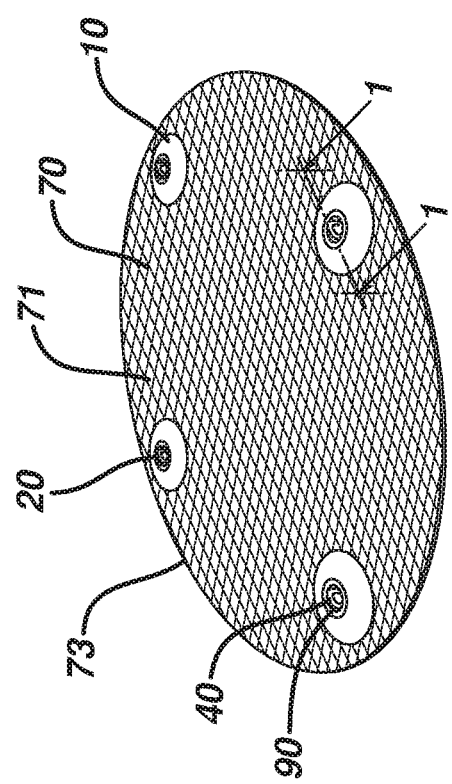
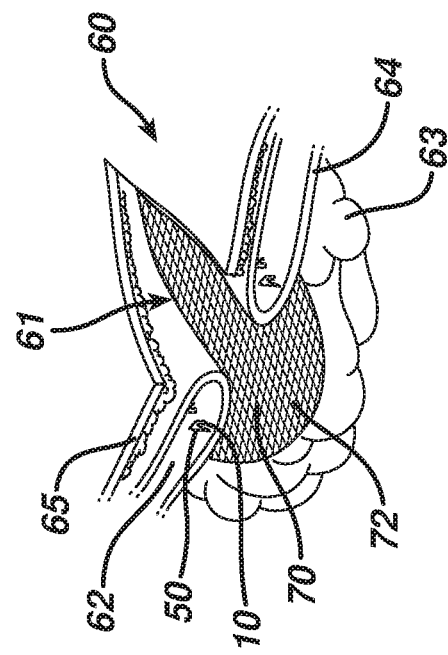

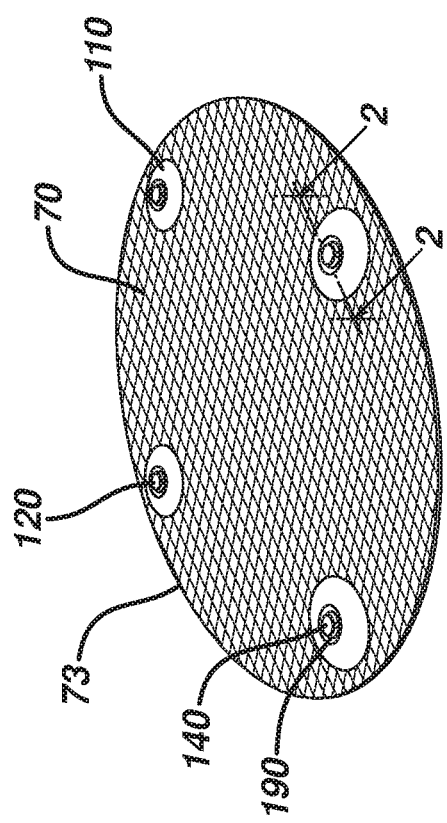

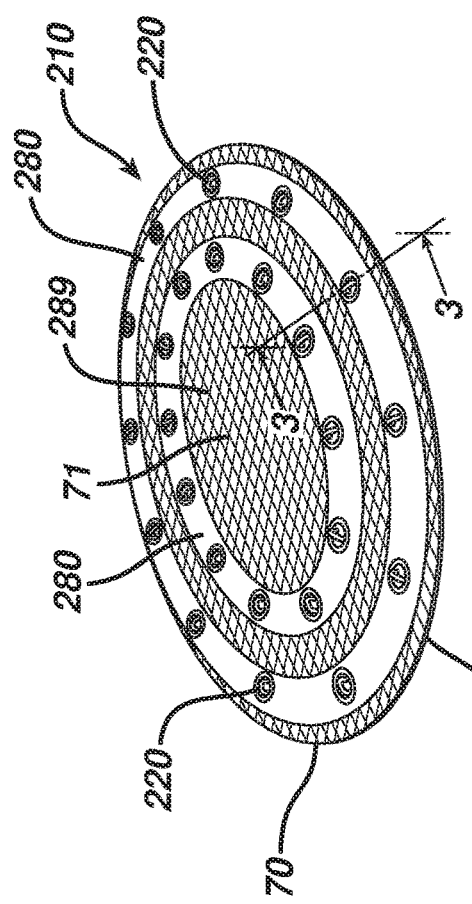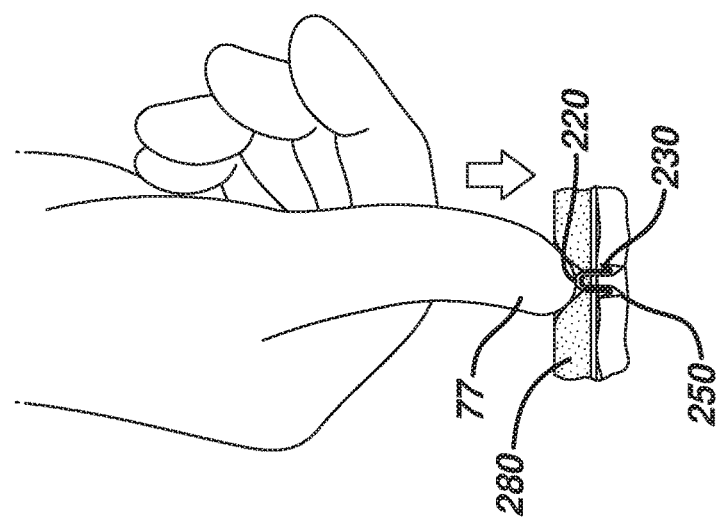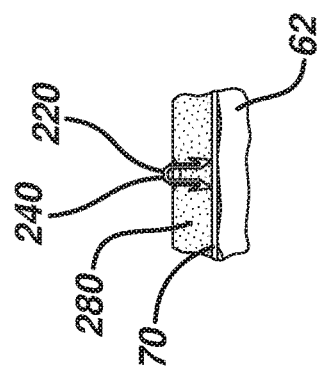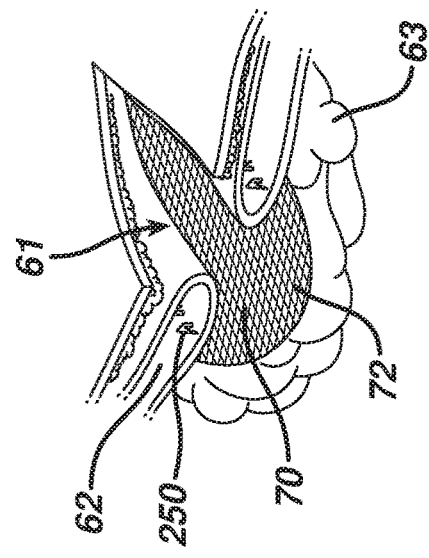
FIG. 3A
FIG. 3C
FIG. 3D
FIG. 3E

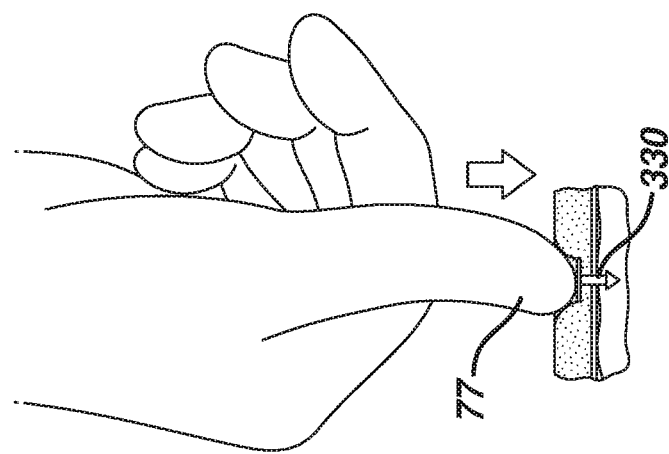
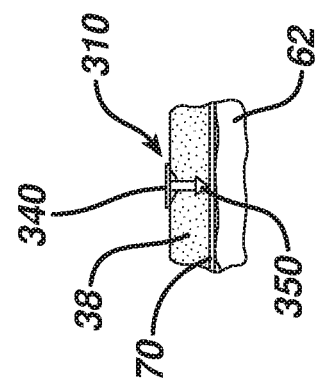
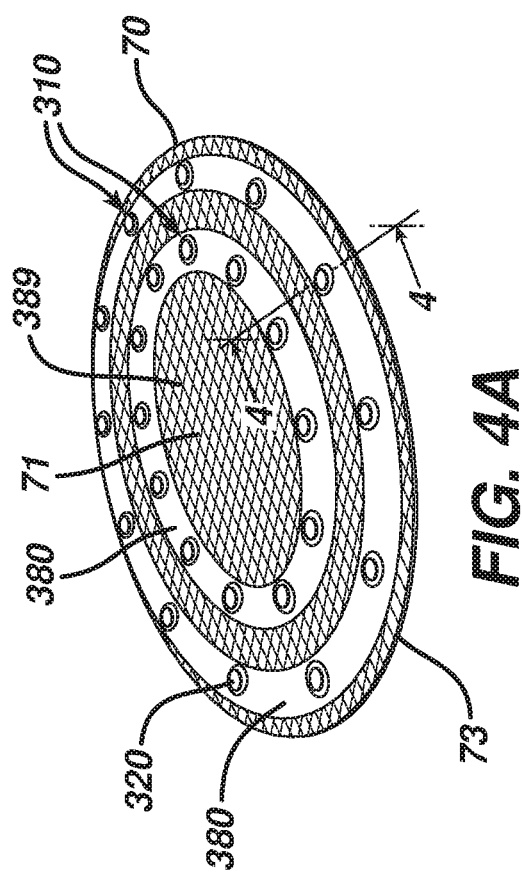
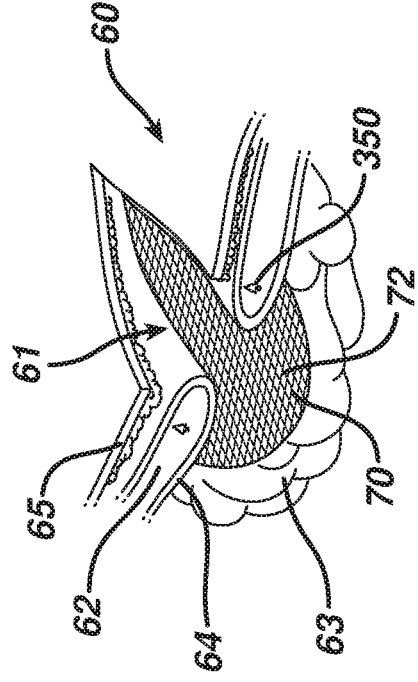

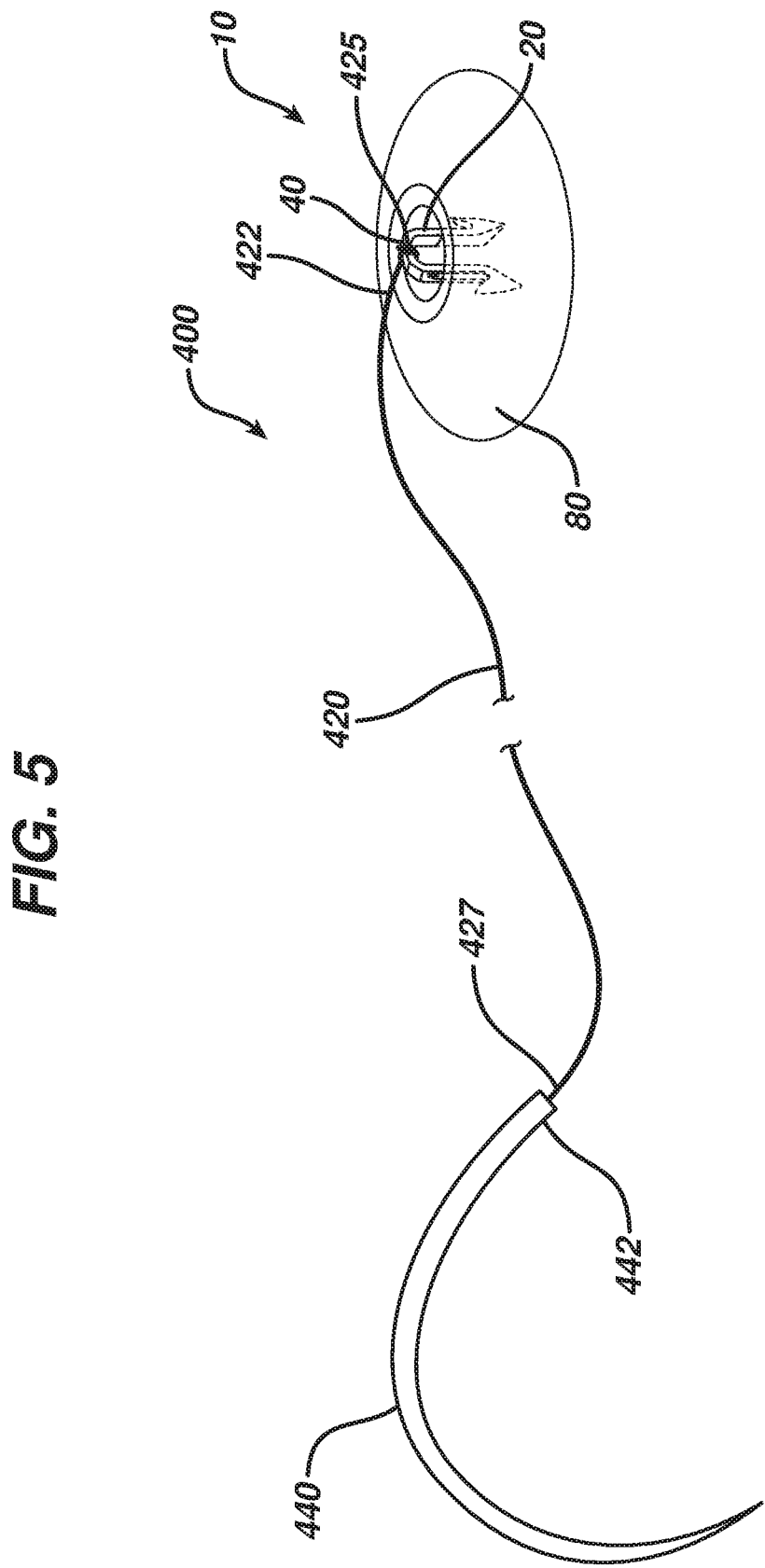

RECESSED SURGICAL FASTENING DEVICES

CROSS REFERENCE TO RELATED APPLICATION

This application is a continuation of co-pending U.S. application Ser. No. 14/082,432 filed on Nov. 18, 2013, the entire disclosures of which are hereby incorporated in their entirety.

TECHNICAL FIELD

The field of art to which this invention relates is medical devices, more particularly, surgical fastening devices for use in surgical procedures.

BACKGROUND OF THE INVENTION

Surgical fastening devices are used in conventional surgical procedures to perform various critical functions. The functions may include soft tissue approximation, bone approximation, fixation or repair of organs, and the fixation of medical devices such as meshes to tissue. The various types of conventional fixation devices that are used in such surgical procedures include sutures, staples, screws, and tacks. Tacks have several advantages that provide particular utility in surgical procedures. The advantages include ease and rapidity of implantation, the ability to be readily implanted in minimally invasive procedures, holding force, etc. Surgical tacks are especially useful in hernia repair procedures, where it is necessary to secure a hernia repair mesh to the peritoneum or other body tissue to effect repair of a hernia defect. The tacks may have several configurations, however a particularly useful configuration is a strap-type tack having two legs with distal piercing members, where the legs are connected by a proximal strap member. Other variations include tacks having a head and a distally extending piercing member. The tacks are typically dispensed by a tack applier instrument loaded with a plurality of tacks that are fired or dispensed by the surgeon about the periphery of the hernia repair mesh. Typically, conventional surgical tacks cannot be dispensed without a tack applier instrument. In addition, the surgeon may have a need for only one or two tacks to fasten a mesh to tissue, but typically conventional tack applier instruments are loaded with a plurality of tacks. Since the tack appliers and tacks cannot be re-sterilized when using absorbable tacks, the unused tacks are wasted.

Although the surgical tacks and tack applier instruments known in the art are adequate for their intended purpose and use, there is a constant need in this art for improved surgical tacks. In particular, singulated tacks that can readily be applied by the surgeon without a tack applier instrument that may be useful adjuncts in tissue repair procedures.

SUMMARY OF THE INVENTION

Accordingly, novel recessed surgical fastening devices are disclosed. The fastening devices have a compressible containment member having a top surface and a bottom surface. A fastening or tack element is at least partially disposed within the compressible containment member. The fastening or tack element has a top and at least one elongated piercing member extending distally from the top. The fastening or tack element is situated within the compressible containment member such that the at least one piercing member is at least partially contained within the compressible containment member. A force applied to the tack device causes the piercing member or members to extend at least partially out from the compressible containment member to engage tissue.

Another aspect of the present invention is a method of performing a surgical procedure, such as repairing a tissue defect. Initially, a recessed surgical fastening device is provided. The fastening device has a compressible containment member having a top surface and a bottom surface. A fastening or tack element is at least partially disposed within the compressible containment member. The fastening element has a top and at least one elongated piercing member extending distally from the top. The fastening element is situated within the compressible containment member such that the at least one piercing member is at least partially contained within the compressible containment member, and, a force applied to the tack device causes the piercing member to extend at least partially out from the compressible containment member to engage tissue. Then, the fastening device is applied to tissue by placing the bottom surface of the device against tissue or a medical device, and applying force to the top of the fastening device, thereby causing the distal piercing member or members to exit at least partially from the compressible containment member to engage underlying tissue.

Yet another aspect of the present invention is a combination of the previously-described surgical fastening device and a surgical needle and suture and a method of using said combination.

These and other aspects and advantages of the present invention will become more apparent from the following description and accompanying drawings.

BRIEF DESCRIPTION OF THE DRAWINGS

FIG. 1A is a perspective view illustrating the bottom side of a tissue repair mesh implant in which surgical fastening devices of the present invention have been mounted.

FIG. 1C illustrates a partial cross-section of a surgical fastening device of FIG. 1A taken along view line 1-1, showing the device in a pre-deployment position.

FIG. 1D illustrates the surgical fastening device of FIG. 1C positioned over tissue with a surgeon's thumb engaging the top of the device and driving the piercing member of the tack element partially into underlying tissue.

FIG. 1E is a perspective view of the hernia mesh implant of FIG. 1A mounted in place over a body wall defect adjacent to tissue with the surgical fastening devices of the present invention; the piercing members are seen extending into and engaging the body wall tissue.

FIG. 2A is a perspective view illustrating the bottom side of a tissue mesh implant in which securement surgical fastening devices of the present invention have been mounted.

FIG. 2C illustrates a partial cross-section of a surgical fastening device of FIG. 2A taken along view line 2-2, showing the device in a pre-deployment position.

FIG. 2D illustrates the surgical fastening device of FIG. 2C positioned over tissue with a surgeon's thumb engaging the top of the device and driving the piercing member of the tack element partially into underlying tissue.

FIG. 2E is a partial perspective cross-sectional perspective view of the tissue repair mesh implant of FIG. 2A mounted in place over a body wall defect adjacent to tissue with the surgical fastening devices of the present invention; the piercing members are seen extending into and engaging the body wall tissue.

FIG. 3A is a perspective view illustrating the bottom side of a tissue repair mesh implant in which an alternate embodiment of a surgical fastening device of the present invention has been mounted; the surgical fastening device is seen to have an oval ring-like configuration and have a plurality of fastening or tack elements.

FIG. 3C illustrates a partial cross-section of the device of FIG. 3A taken along view line 3-3, showing the device in a pre-deployment position. The fastening device is seen to have a plurality of fastening or tack elements each tack element having two elongated piercing members connected by a bridge member.

FIG. 3D illustrates the surgical fastening device of FIG. 3C positioned over tissue with a surgeon's thumb engaging the top of the device adjacent to a tack element and driving the piercing members of the tack element partially into underlying tissue.

FIG. 3E is a partial cross-sectional perspective view of the tissue repair mesh implant of FIG. 3A mounted in place over a body wall defect adjacent to tissue with the surgical fastening device of FIG. 3A; the piercing members are seen extending into and engaging underlying tissue.

FIG. 4A is a perspective view illustrating the bottom side of a hernia mesh implant in which an alternate embodiment of a surgical fastening device of the present invention has been mounted; the device is seen to have an oval ring-like configuration and have a plurality of fastening or tack elements.

FIG. 4C illustrates a partial cross-section of the surgical fastening device of FIG. 4A taken along view line 4-4, showing the device in a pre-deployment position; the surgical fastening device is seen to have a plurality of fastening or tack elements each having a single elongated piercing member extending from a top head member.

FIG. 4D illustrates the surgical fastening device of FIG. 4C positioned over tissue with a surgeon's thumb engaging the top of the device adjacent to a tack element and driving the piercing member of the tack element partially into underlying tissue.

FIG. 4E is a partial cross-sectional perspective view of the tissue repair mesh implant of FIG. 4A mounted in place over a body wall defect adjacent to tissue with the surgical fastening device of FIG. 4A; the piercing members are seen extending into and engaging underlying tissue.

FIG. 5 is a perspective view of a surgical fastening device of the present invention having a surgical suture and needle mounted to the device.

DETAILED DESCRIPTION OF THE INVENTION

Figure 1B:
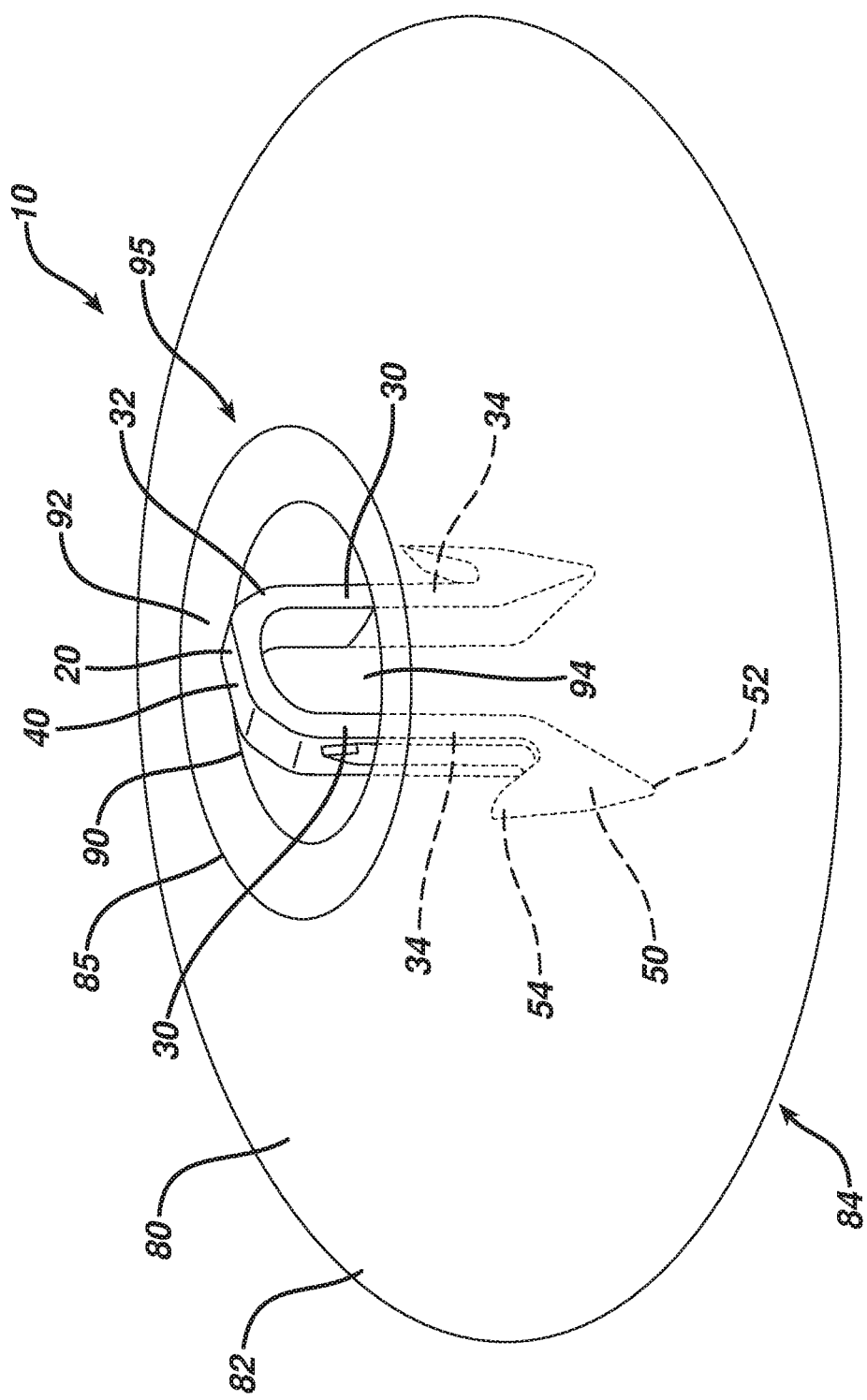
FIG. 1B is a perspective view of a surgical fastening device of FIG. 1A; the surgical fastening device is seen to have a fastening or tack element having two elongated piercing members connected by a bridge member.

The novel recessed surgical fastening devices of the present invention may be made from various biocompatible materials that are suitable for implantation. The materials include biocompatible non-absorbable materials and biocompatible, absorbable materials. It is particularly preferred to manufacture the recessed tack devices of the present invention from biocompatible absorbable materials. The tack devices, as described herein, have a fastening or tack element that is least partially contained with a containment member.

The tack members of the present invention may be made from a variety of absorbable polymers. They include the homopolymers of glycolide, L(−)-lactide, D(+)-lactide, meso-lactide, trimethylene carbonate, p-dioxanone, and ε-caprolactone and their corresponding copolymers in any proportion. It is to be understood that the term copolymer will include polymers made by a plurality of monomer type, without limit. The tack members of the present invention may also be made blends of the aforementioned homo- and copolymers. Of particular utility are the blends of poly(p-dioxanone) and the lactide-rich, lactide/glycolide copolymers, especially 85/15 poly[L(−)lactide-co-glycolide].

The containment members of the fastening devices of the present invention may be foams or hydrogels made from, for example, polyoxaesters, the homopolymers of glycolide, L(−)-lactide, D(+)-lactide, meso-lactide, trimethylene carbonate, p-dioxanone, and ε-caprolactone and their corresponding copolymers in any proportion. The following absorbable polymers are useful: polylactones, polyglycolides, polycaprolactones, polydioxanones, trimethylene carbonates, polyoxaesters, and any corresponding co-polymers of one or more of the aforementioned polymers. Of particular utility are the corresponding polymers and copolymers possessing glass transitions temperatures low enough to produce soft, yet resilient, containment members. Of further utility are the polymers and copolymers possessing dimensional stability. One way of achieving dimensional stability in polymers and copolymers possessing glass transitions temperatures is through crystallization.

The novel recessed fastening devices of the present invention may be made using conventional manufacturing processes and processing equipment. The processes may include molding, casting, lyophilization, cutting, stamping, machining, and the like and combinations thereof.

A recessed fastening device of the present invention may be made and assembled in a conventional process, for example, embedding a pre-formed tack into a lyophilized foam member or a hydrogel member, casting a foam or hydrogel in a mold containing a securement tack, etc.

Strap-like surgical tacks having particular utility in tissue repair procedures, such as hernia repairs, are disclosed in commonly owned U.S. patent application Ser. No. 12/464, 143 which is incorporated by reference.

Referring to FIGS. 1A-E, a novel surgical recessed fastening device 10 of the present invention is seen. The device 10 functions as a securement fastener or tack. The fastening device 10 is seen to have a fastening or tack element 20 and a containment member 80. The tack element 20 is seen to have a pair of downwardly extending leg members 30. The leg members 30 are seen to have proximal ends 32 and distal ends 34. Extending from the distal ends 34 are piercing points 50. Piercing points 50 are seen to have distal piercing points 52 and barbs 54. The piercing points 50 may have other conventional configurations including, double or multiple barbs, ridges, hooks cogs, and the like. The cross-member 40 is seen to extend between the leg members 30 and to connect the leg members 30 at the proximal ends 32. The leg members 30 and the cross-member 40 may have a variety of cross-sections, including square, rectangular, circular, oval, polygonal, combinations thereof and the like. The leg members 30 may be straight, curved or angulated. Similarly, the cross-member 40 may be straight, curved, or angulated. The recessed tack device 10 is seen to be partially contained by the containment member 80. Containment member 80 is seen to have a substantially hemispherical or dome shaped configuration, but may have other geometric shapes including cylindrical, cubic, frustoconical, prismatic, rhombic, pyramidal, spherical, combinations thereof and the like. Member 80 is seen to have top side 82 and bottom side 84. Preferably, bottom side 84 is flat, but may be if desired curved, angulated, etc. Containment member 80 is also seen to have top section 85 containing cavity 90. Cavity 90 is seen to have a generally hemispherical configuration bounded by side wall 92 and having bottom section 94. Cavity 90 is seen to have top opening 95. Cavity 90 may have other geometric configurations including cylindrical, semi-cubic, etc. The tack element 20 is mounted in the containment member 80 such that the distal ends 34 of the leg members 32 and the piercing points 50 are contained within the member 80, while the proximal ends of the leg members 30 and cross-member 40 are contained within cavity 90. If desired, although not illustrated, the entire lengths of leg members 30 may be contained within member 80, with only the cross-member 40 positioned in cavity 90, or the entire fastening or tack element 20 may be contained within containment member 80 with no section or part of element 20 within cavity 90. In addition, optionally the cavity 90 may be eliminated from the device 10. Containment member 80 is a compressible material that will permit the piercing points 50 of the tack element 20 to extend out through the bottom 84 or sides of the containment member 80.

A tissue defect repair mesh 70 useful to repair tissue defects in body walls such as hernias is illustrated in FIGS. 1A-E. The mesh 70 is seen to have bottom side 71, top side 72 and outer periphery 73. A schematic of a hernia tissue defect in an abdominal body wall is also illustrated in FIG. 1E. The defect 60 is seen to have opening 61 extending through body wall 62. Underlying viscera 63 are illustrated below body wall defect 60. Also seen are the interior peritoneum 64 on the inner side of body wall 62 and the outer dermal layers 65.

The recessed surgical fastening devices of the present invention may be used in the following manner. The surgeon or an assistant will remove a device 10 from a sterile package. Referring to FIGS. 1A-E, the device 10 is grasped by the surgeon such that one of the surgeon's fingers, such as the thumb 77 or other finger, engages the top section 85 of containment member 80 and cross-member 40. The surgeon then positions the device 10 such that the bottom side 84 of element 80 is in contact with tissue or a medical device, such as a hernia mesh device 70 that is in contact with tissue wall 62. The surgeon then manually presses with a finger such as thumb 77 on the top of the device 10, engaging cross-member 40 and causing the containment member 80 to at least partially compress or deform and allow the legs 30 and piercing points 50 of the tack element 20 to move through and at least partially exit the bottom side 84 of member 80, and penetrate mesh 70 and peritoneum 64 such that the piercing points 50 and at least the distal sections 34 of leg members 30 are lodged in the tissue of body wall 62. As seen in FIG. 1A, four devices 10 of the present invention are used to secure or fasten mesh 70 to peritoneum 64 and body wall 62. If desired by the surgeon, or if required to further secure mesh 70 in order to repair defect 60, additional fastening devices 10 may be emplaced about the periphery 73 of mesh 70. Alternatively, the devices 10 may be used to "tack" or position the mesh 70 in place on the peritoneal surface 64 of body wall 62 adjacent to defect 60, and the surgeon may use conventional tacking devices and tacks and/or sutures to complete the affixation of mesh 70 to the body wall 62 to repair tissue defect 60.

An alternate embodiment of a novel surgical recessed fastening or tack device 110 of the present invention is seen in FIGS. 2A-E. The device 110 functions as a securement fastener or tack. The tack device 110 is seen to have a fastening or tack element 120 and a containment member 180. The fastening or tack element 120 is seen to have a downwardly extending leg member 130. The leg member 130 is seen to have proximal end 132 and distal end 134. Extending from the distal end 134 is the piercing point 150. Piercing point 150 is seen to have distal piercing point 152 and barb or barbs 154. The piercing point 150 may have other conventional configurations including, single or multiple barbs (i.e., in excess of two), ridges, hooks, cogs and the like. The tack head member 140 is seen to be a disk-like member mounted to the proximal end 132 of leg member 130 such that leg member 130 extends away from the bottom side 141 of tack head member 140. The leg member 130 may have a variety of cross-sections, including square, rectangular, circular, oval, polygonal, combinations thereof and the like. The tack head member 140 may have a variety of shapes including square, oval, circular, rectangular, etc. The top side 142 of tack head member 140 may be raised (e.g., curved), convex, concave, or flat. The leg members 132 may be straight, curved or angulated. The recessed fastening or tack device 110 is seen to be partially contained by the containment member 180. Containment member 180 is seen to have a substantially hemispherical or dome shaped configuration, but may have other geometric shapes including cylindrical, cubic, frustoconical, prismatic, rhombic, pyramidal, spherical, combinations thereof and the like. Member 180 is seen to have top side 182 and bottom side 184. Preferably, bottom side 184 is flat, but may be if desired curved, angulated, etc. Containment member 180 is also seen to have top section 185 containing cavity 190. Cavity 190 is seen to have a generally hemispherical configuration bounded by side wall 192 and having bottom section 194. Cavity 190 is seen to have top opening 195. Cavity 90 may have other geometric configurations including cylindrical, semi-cubic, etc. The tack element 120 is mounted in the containment member 180 such that the distal end 134 of the leg member 130 and the piercing point 150 are contained within the member 180, while the proximal end of the leg member 130 and tack head member 140 are contained within cavity 190. If desired, although not illustrated, the entire length of leg member 130 may be contained within member 180 with only the tack head member 140 positioned within cavity 190, or the entire tack element 120 may be contained within member 180 with no section or part of tack element 120 contained in cavity 190. In addition, optionally the cavity 190 may be eliminated from the device 110. Containment member 180 is a compressible material that will permit the piercing point 150 of the tack element 120 to extend out through the bottom 184 or sides of the containment member 180.

A tissue defect repair mesh 70 useful to repair tissue defects in body walls such as hernias is illustrated in FIGS. 2A-E. The mesh 70 is seen to have bottom side 71, top side 72 and outer periphery 73. A schematic of a hernia tissue defect in an abdominal body wall is also illustrated in FIGS. 2A-E. The defect 60 is seen to have opening 61 extending through body wall 62. Underlying viscera 63 are illustrated below body wall defect 60. Also seen are the interior peritoneum 64 on the inner side of body wall 62 and the outer dermal layers 65.

Figure 2B:
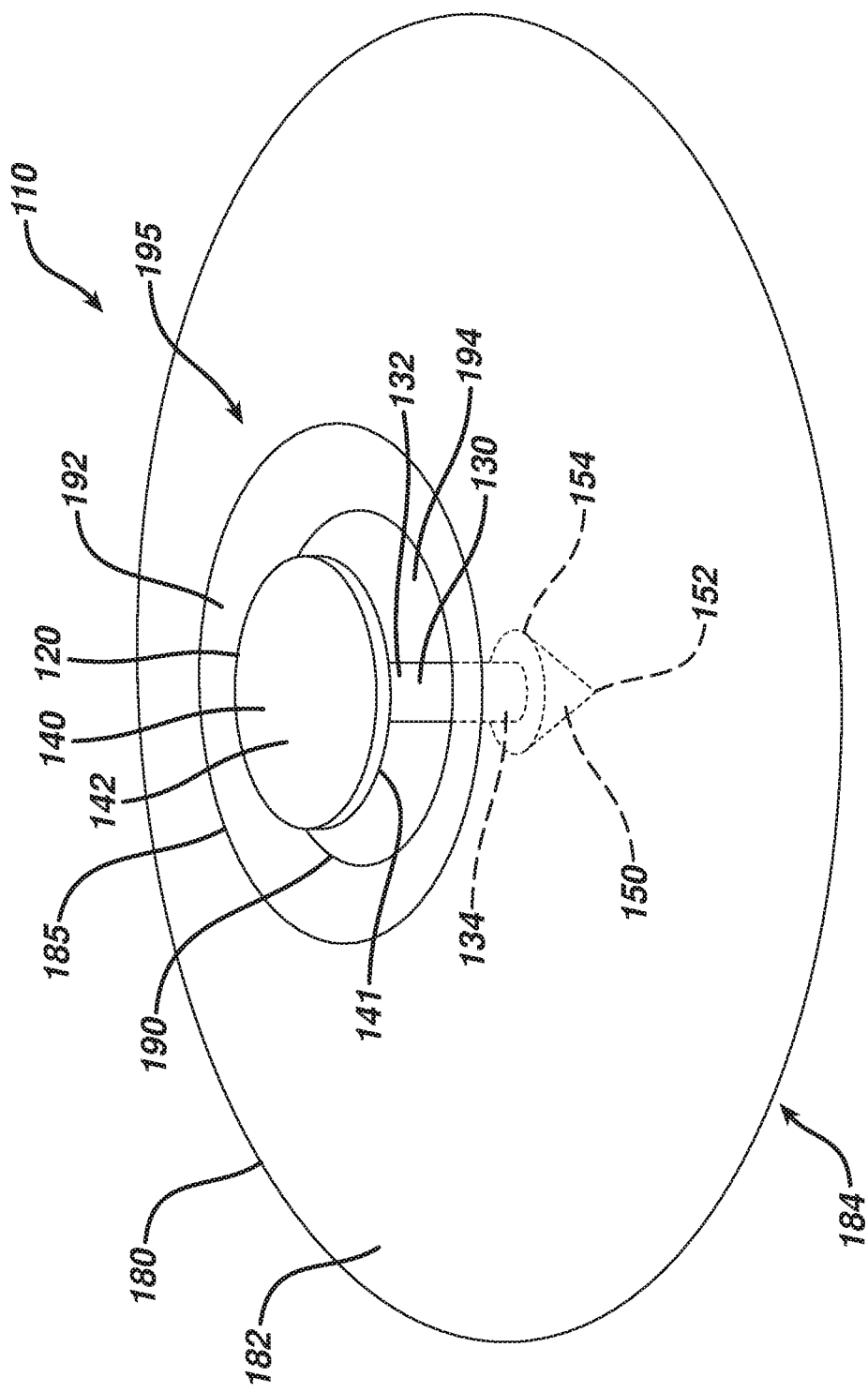
FIG. 2B is a perspective view of a securement surgical fastening device of FIG. 2A; the surgical fastening device is seen to have a fastening or tack element having an elongated piercing member extending from a top head member.

The recessed surgical fastening or tack device 110 of the present invention may be used in the following manner. The surgeon or an assistant will remove a device 110 from a sterile package. Referring to FIGS. 2A-E, the device 110 is grasped by the surgeon such that one of the surgeon's fingers, such as the thumb 77 or other finger, engages the top section 185 of containment member 180 and tack head member 140. The surgeon then positions the device 110 such that the bottom side 184 of containment element 180 is in contact with tissue or a medical device, such as a hernia mesh device 70 that is in contact with tissue wall 62. The surgeon then manually presses with a finger, such as thumb 77, on the top of the device 110, engaging tack head member 140 and causing the containment member 180 to at least partially compress or deform and allow the leg 130 and the piercing point 150 of the tack element 120 to move through and at least partially exit the bottom side 184 of member 180, and penetrate mesh 70 and peritoneum 64 such that the piercing point 150 and at least the distal section 134 of leg member 130 is lodged in the tissue in body wall 62. As seen in FIG. 2A, four devices 110 of the present invention are used to secure or fasten mesh 70 to peritoneum 64 and body wall 62. If desired by the surgeon, or if required to further secure mesh 70 in order to repair defect 60, additional fastening or tack devices 110 may be emplaced about the periphery 73 of mesh 70. Alternatively, the devices 110 may be used to "tack" or position the mesh 70 in place on the peritoneal surface 64 body wall 62 adjacent to defect 60, and the surgeon may use conventional tacking devices and tacks and/or sutures to complete the affixation of mesh 70 to the body wall 62 to repair tissue defect 60.

An alternative embodiment 210 of the fastening or tack devices of the present invention containing multiple fastening or tack elements 220 is seen in FIGS. 3A-3E. The recessed tack device 210 is seen to have an annular or ring-shaped containment member 280. The containment member 280 is seen to have top side 282 and bottom side 284. Preferably, bottom side 284 is flat, but may be if desired curved, angulated, etc. Containment member 280 is seen to have a generally oval shape, with an oval opening 289. The containment member 280 may have other shapes including circular, square, rectangular, etc., and combinations thereof, and, the opening 289 may be similarly shaped. Containment member 280 is seen to have a generally rectangular cross-section, but may have other geometric cross-sections including circular, elliptical, semi-circular, square, oval, rectangular, polygonal, curved, combinations thereof, and the like. Containment member 280 is also seen to have top sections 285 containing a plurality of cavities 290. Each cavity 290 is seen to have a generally hemispherical configuration bounded by side wall 292 and having bottom section 294. Each cavity 290 is seen to have top opening 195. The cavities 190 may have other geometric configurations including cylindrical, semi-cubic, etc. The fastening or tack device 210 is seen to have fastening or tack elements 220 mounted to containment member 280. Each tack element 220 is seen to have a pair of downwardly extending leg members 230. The leg members 230 are seen to have proximal ends 232 and distal ends 234. Extending from the distal ends 234 are piercing points 250. Piercing points 250 are seen to have distal piercing points 252 and barbs 254. The piercing points 250 may have other conventional configurations including, double or multiple barbs, ridges, hooks cogs, and the like. The cross-member 240 is seen to extend between the leg members 230 and to connect the leg members 230 at the proximal ends 232. The leg members 230 and the cross-member 240 may have a variety of cross-sections, including square, rectangular, circular, oval, polygonal, combinations thereof and the like. The leg members 230 may be straight, curved or angulated. Similarly, the cross-member 240 may be straight, curved, or angulated. The tack members 220 are mounted in the containment member 280 such that the distal ends 234 of the leg members 230 and the piercing points 250 are contained within the member 280, while the proximal ends 232 of the leg members 230 and the engaging cross-member 240 are contained within cavity 290. If desired, although not illustrated, the entire length of the leg members 230 may be contained within member 280 with only the engaging cross-member 240 positioned within cavity 290, or the entire tack element 220 may be contained within member 280 with no section or part of a tack element 220 contained in a cavity 290. In addition, optionally the cavities 290 may be eliminated from the device 210. Containment member 280 is a compressible material that will permit the piercing points 250 of the tack elements 20 to extend out through the bottom 284 or sides of the containment member 280.

A tissue defect repair mesh 70 useful to repair tissue defects in body walls such as hernias is illustrated in FIGS. 3A-E. The mesh 70 is seen to have bottom side 71, top side 72 and outer periphery 73. A schematic of a hernia tissue defect in an abdominal body wall is also illustrated in FIGS. 3A-E. The defect 60 is seen to have opening 61 extending through body wall 62. Underlying viscera 63 are illustrated below body wall defect 60. Also seen are the interior peritoneum 64 on the inner side of body wall 62 and the outer dermal layers 65.

Figure 3B:
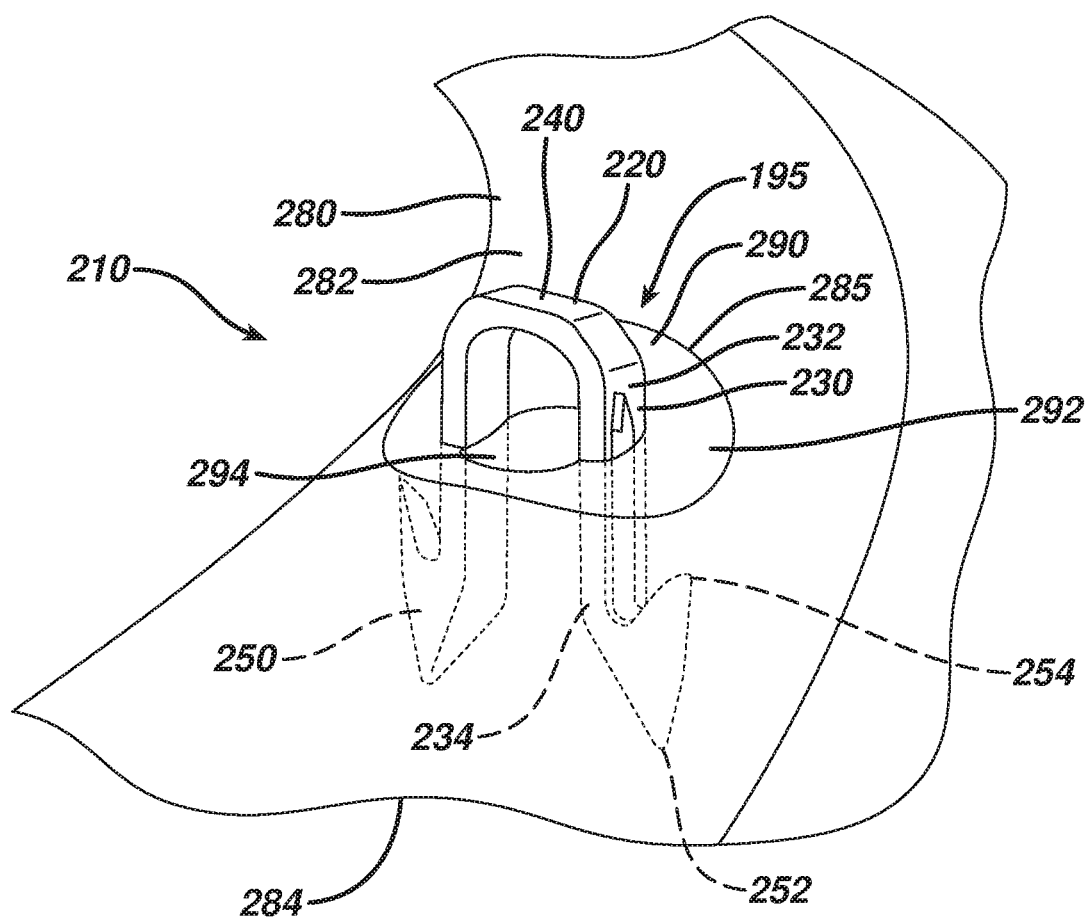
FIG. 3B is a magnified partial section of the surgical fastening device of FIG. 3A.

The recessed surgical fastening or tack devices 210 of the present invention may be used in the following manner. The surgeon or an assistant will remove a device 210 from a sterile package. Referring to FIGS. 3A-E, the device 210 is grasped by the surgeon such that one of the surgeon's fingers, such as the thumb 77 or other finger, engages a top section 285 of containment member 280 and cross-member 240. The surgeon then positions the device 210 such that the bottom side 284 of containment member 280 is in contact with tissue or a medical device, such as a hernia mesh device 70 that is in contact with tissue wall 62. The surgeon then manually presses with a finger, such as thumb 77, on the top of each tack element 220, engaging cross-member 240 and causing the containment member 280 to at least partially compress or deform and allow the legs 230 and piercing points 250 of the tack elements 220 to move through and at least partially exit the bottom side 284 of member 280, and penetrate mesh 70 and peritoneum 64 such that the piercing points 250 and at least the distal sections 234 of leg members 230 are lodged in the tissue of body wall 62. This is repeated for each tack element 220, until all of the tack elements 220 are secured to the underlying tissue of body wall 62 about the containment member 280. As seen in FIG. 3A, two devices 210 of the present invention are used to secure mesh 70 to peritoneum 64 and body wall 62. The devices 210 are seen to have different overall sizes such that they can be mounted concentrically to effect a "double crown" repair. However, alternately, a single device 210 could be utilized. If desired by the surgeon, or if required to further secure mesh 70 in order to repair defect 60, additional tack devices 210 may be emplaced about mesh 70 in a similar concentric manner. Alternatively, the surgeon may use as an adjunct with the tack device 210 conventional tacking devices and tacks and/or sutures to complete the affixation of mesh 70 to the body wall 62 to repair tissue defect 60.

An alternative embodiment of the recessed surgical fastening or tack devices present invention containing multiple tack elements 320 is seen in FIGS. 4A-E. The recessed fastening or tack device 310 is seen to have an annular or ring shaped containment member 380. The containment member 380 is seen to have top side 382 and bottom side 384. Preferably, bottom side 384 is flat, but may be if desired curved, angulated, etc. Containment member 389 is seen to have a generally oval shape, with an oval opening 389. The ring member 380 may have other shapes including circular, square, rectangular, etc., and combinations thereof, and, the opening 389 may be similarly shaped. Containment member 380 is seen to have a generally rectangular cross-section, but may have other geometric cross-sections including circular, elliptical, semi-circular, square, oval, rectangular, polygonal, curved, combinations thereof, and the like. Containment member 380 is also seen to have top sections 385 containing a plurality of cavities 390. Each cavity 390 is seen to have a generally hemispherical configuration bounded by side wall 392 and having bottom section 394. Each cavity 390 is seen to have top opening 395. The cavities 390 may have other geometric configurations including cylindrical, semi-cubic, etc. The fastening or tack elements 320 are seen to have downwardly extending leg member 330. Each leg member 330 is seen to have proximal end 332 and distal end 334. Extending from the distal end 334 is piercing point 350. Piercing point 350 is seen to have distal piercing point 352 and barb or barbs 154. The piercing points 350 may have other conventional configurations including, single or multiple barbs (i.e., in excess of two), ridges, hooks cogs, and the like. The tack head member 340 is seen to be a disk-like member mounted to the proximal end 332 of leg member 330 such that leg member 330 extends away from the bottom side 341 of tack head member 340. The leg member 330 may have a variety of cross-sections, including square, rectangular, circular, oval, polygonal, combinations thereof and the like. The tack head member 340 may have a variety of shapes including square, oval, circular, rectangular, etc. The top side 342 of tack head member 340 may be raised (e.g., curved), convex, concave, or flat. The leg members 330 may be straight, curved or angulated. The tack elements 320 are mounted in the containment member 380 such that the distal ends 334 of the leg members 330 and the piercing points 350 are contained within the member 380, while the proximal ends 332 of the leg members 330 and the tack head member 340 are contained within cavity 390. If desired, although not illustrated, the entire length of each leg member 330 may be contained within member 380 with only the tack head member 340 positioned within cavity 390, or each entire tack element 320 may be contained within member 380 with no section or part of a tack element 320 contained in a cavity 390. In addition, optionally the cavities 390 may be eliminated from the device 310. Containment member 380 is a compressible material that will permit the piercing points 350 of the tack elements 320 to extend out through the bottom 384 or sides of the containment member 380.

A tissue defect repair mesh 70 useful to repair tissue defects in body walls such as hernias is illustrated in FIGS. 4A-E. The mesh 70 is seen to have bottom side 71, top side 72 and outer periphery 73. A schematic of a hernia tissue defect in an abdominal body wall is also illustrated in FIGS. 4A-E. The defect 60 is seen to have opening 61 extending through body wall 62. Underlying viscera 63 are illustrated below body wall defect 60. Also seen are the interior peritoneum 64 on the inner side of body wall 62 and the outer dermal layers 65.

Figure 4B:
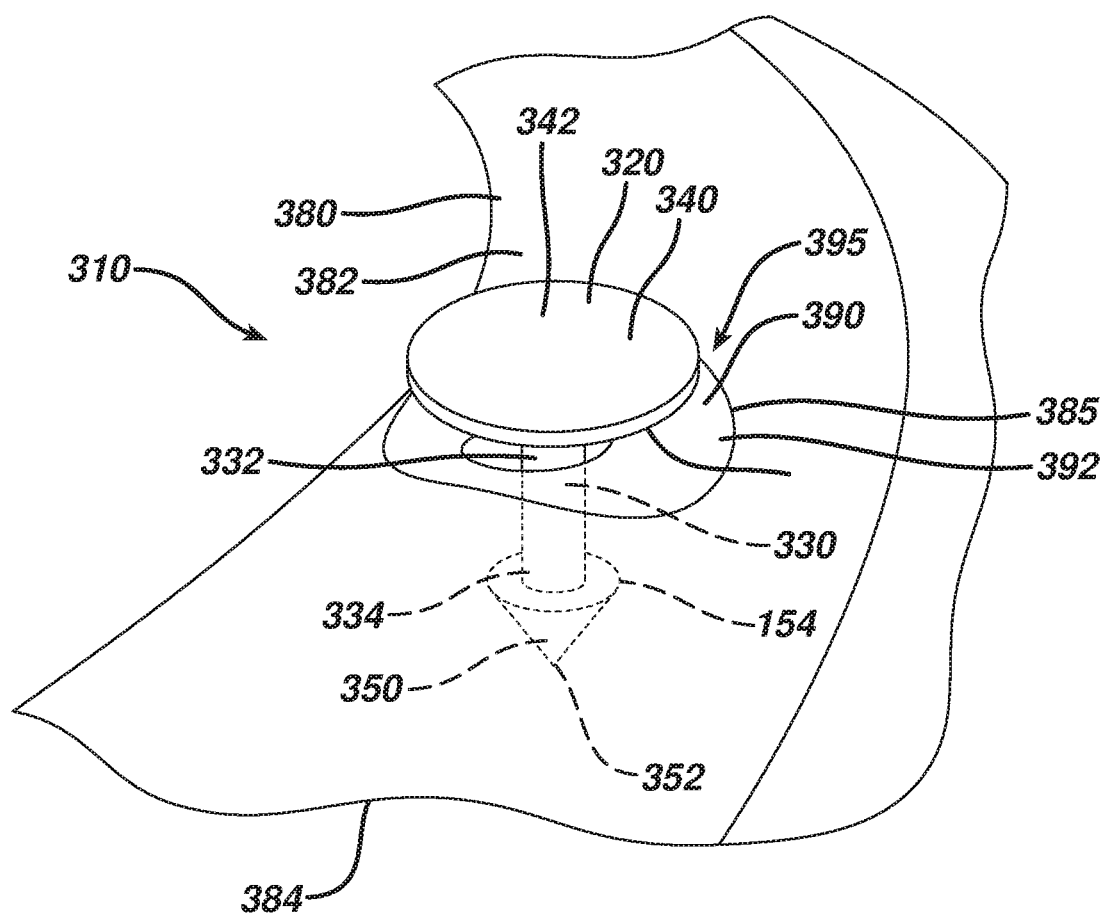
FIG. 4B is a magnified partial section of the device of FIG. 4A.

The recessed surgical fastening or tack devices 310 of the present invention may be used in the following manner. The surgeon or an assistant will remove a device 310 from a sterile package. Referring to FIGS. 4A-E, the device 310 is grasped by the surgeon such that one of the surgeon's fingers, such as the thumb 77, engages a top section 385 of containment member 380 and tack head member 140. The surgeon then positions the device 310 such that the bottom side 384 of containment member 380 is in contact with tissue or a medical device, such as a hernia mesh device 70 that is in contact with tissue wall 62. The surgeon then manually presses with a finger, such as thumb 77, on the top of each fastening or tack element 320, engaging tack head member 340 and causing the containment member 380 to at least partially compress or deform and allow the legs 330 and piercing points 350 of the tack elements 320 to move through and at least partially exit the bottom side 384 of member 380, and penetrate mesh 70 and peritoneum 64 such that the piercing points 350 and at least the distal sections 334 of leg members 330 are lodged in the tissue of body wall 62. This is repeated for each tack element 320, until all of the tack elements 320 are secured to the underlying tissue of body wall 62 about the containment member 380. As seen in FIG. 4A, two devices 310 of the present invention are used to secure mesh 70 to peritoneum 64 and body wall 62. The devices 310 are seen to have different overall sizes such that they can be mounted concentrically to effect a "double crown" repair. However, alternately, a single device 310 could be utilized. If desired by the surgeon, or if required to further secure mesh 70 in order to repair defect 60, additional tack devices 310 may be emplaced about mesh 70 in a similar concentric manner. Alternatively, the surgeon may use as an adjunct with the tack device 310 conventional tacking devices and tacks and/or sutures to complete the affixation of mesh 70 to the body wall 62 to repair defect 60.

Figure 6:
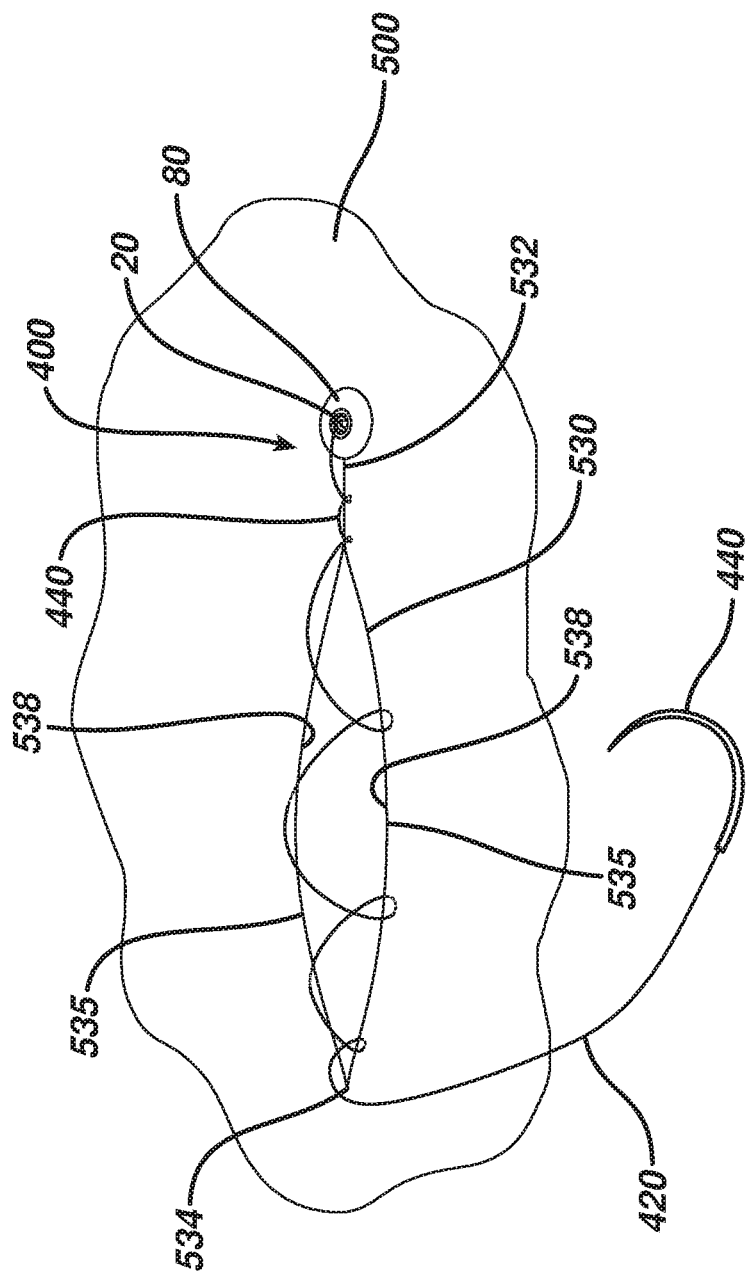
FIG. 6 is a plan view illustrating the combination of the surgical needle, surgical suture and fastening device of FIG. 5 utilized in a surgical procedure to repair a wound or incision in tissue.

Referring to FIGS. 5 and 6, another embodiment of the present invention is illustrated. The combination 400 is seen to consist of a fastening device 10 of the present invention with a surgical suture 420. Surgical suture 420 is seen to have proximal end 422 and distal end 427. The distal end 427 is seen to be mounted to the proximal end 442 of surgical needle 440. The proximal end 422 of suture 420 is secured to the fastening element 10 by knotting the end 422 to the cross-member 40 of fastening or tack element 20 by forming surgical knot 425. The suture 420 may be mounted to the device 10 in other conventional manners, including, for example gluing, welding, co-molding, etc. The suture 420 may be mounted to tack element 20, containment member 80, or to both tack element 20 and containment member 80. The suture 420 may be mounted to device 10 either fixedly or slidably, e.g., a suture loop mounted to tack element 20. The combination 400 may be used to suture tissue 500 as seen in FIG. 6. Tissue 500 is seen to have incision 530. The incision 530 has opposed sides 535 having faces 538. The surgeon places the device 10 at one end 532 of incision 500 pushing on the top of the device 10 (i.e., tack element 20 and containment member 80) to secure at least part of the leg member 30 and piercing points 50 and barb members 54 in tissue 500. The surgeon then proceeds to form a mattress-type suture approximation of the tissue about incision 530 along the length of incision 530 by passing the surgical needle into, through and out of the tissue for multiple passes to from stitches 440. The is continued until the surgeon reaches the other end 534 of incision 530 such that the sides 535 and faces 538 are substantially approximated, and the suture 420 is then knotted in a conventional manner to secure it in place. The incision 500 is repaired with combination 400 by utilizing a surgical knot on only one end of the incision 500.

Although not illustrated, the suture 420 may optionally have conventional barbs. The barbs may be formed or applied in a conventional manner, for example including cutting, molding, etc. Although, when barbs are optionally present, it would be preferred for the suture 420 to have a plurality of barbs, it is possible to have a single barb.

The recessed tack devices of the present invention when emplaced in tissue additionally act as a spacer element to help prevent the bottom of a tissue repair mesh or patch from contacting the underlying viscera. The recessed tack devices of the present invention are particularly useful to secure tissue repair devices to tissue, including devices made from tissue fabrics such as meshes, non-wovens, foams, tissue engineering substrates, etc. The recessed tack devices of the present invention also have utility in securing other medical devices and tissue implants to tissue including wound approximating devices, tissue tethering implants, tendons, ligaments, skin, membranes, and the like. In addition, the tissue repair devices of the present invention may be used to approximate tissue in a variety of surgical procedures including, but not limited to, wound closure, body wall defect repair, organ repair and fixation, vessel repair and placement, and the like.

Although this invention has been shown and described with respect to detailed embodiments thereof, it will be understood by those skilled in the art that various changes in form and detail thereof may be made without departing from the spirit and scope of the claimed invention.

We claim:

1. A surgical fastening device, comprising:
   a compressible member having a top surface and a bottom surface, said member having a vertical axis and a horizontal axis, wherein the compressible member comprises an absorbable polymer foam or an absorbable hydrogel; and,
   a fastening element having a vertical axis and being at least partially disposed within the compressible member such that the vertical axis of the fastening element is substantially aligned with the vertical axis of the compressible member, the fastening element having a top and at least one elongated piercing member extending distally from the top, the piercing member having a leg with a proximal end, a distal end, and a piercing point and barb extending from the distal end, the barb configured to engage and lodge in tissue, wherein the top of the fastening element is located adjacent to the top surface of the compressible member, wherein the fastening element is situated within the compressible member such that the at least one piercing member is at least partially contained within the compressible member and configured so that a pressing force applied by a finger directly to the top surface of the compressible member, the top of the fastening element, or both the top surface of the compressible member and the top of the fastening element causes at least part of the distal end of the leg and the piercing point and barb of the at least one piercing member to extend at least partially out from the compressible member to engage and lodge in underlying tissue.

2. The fastening device of claim 1, wherein the fastening element has two elongated piercing members connected by a bridge member.

3. The fastening device of claim 1, wherein the compressible member has a generally cylindrical configuration.

4. The fastening device of claim 1, wherein the fastening element comprises an absorbable polymer.

5. The fastening device of claim 4, wherein the absorbable polymer comprises a polymer selected from the group consisting of homopolymers of glycolide, L(−)-lactide, D(+)-lactide, meso-lactide, trimethylene carbonate, p-dioxanone, and ε-caprolactone and their corresponding copolymers.

6. The device of claim 5, wherein the polymer comprises 85/15 poly [L(−)lactide-co-glycolide].

7. The fastening device of claim 1, wherein the absorbable polymer comprises a polymer selected from the group consisting of polyoxaesters, the homopolymers of glycolide, L(−)-lactide, D(+)-lactide, meso-lactide, trimethylene carbonate, p-dioxanone, and ε-caprolactone, polylactones, polyglycolides, polycaprolactones, polydioxanones, trimethylene carbonates, polyoxaesters, and co-polymers thereof.

8. The fastening device of claim 1, comprising at least one additional fastening member.

9. The fastening device of claim 1, wherein the compressible member has a ring-like configuration.

10. The fastening device of claim 9, wherein the configuration is generally circular.

11. The fastening device of claim 9, wherein the configuration is generally oval.

12. The fastening device of claim 1, additionally comprising a cavity in the top surface of the compressible member.

13. A combination comprising a tissue repair mesh and the surgical fastening device of claim 1.

14. The fastening device of claim 1, additionally comprising a head member mounted to the top of the fastening element.

15. The fastening device of claim 14, wherein the head member has a disk-like shape.

16. A combination comprising the fastening device of claim 1 and a surgical suture.

17. The combination of claim 16, wherein the suture has a surgical needle mounted to at least one end.

18. The device of claim 16, wherein the suture additionally comprises at least one barb.

* * * * *